US011206990B2

(12) United States Patent
Lee et al.

(10) Patent No.: US 11,206,990 B2
(45) Date of Patent: Dec. 28, 2021

(54) DEEP TISSUE FLOWMETRY USING DIFFUSE SPECKLE CONTRAST ANALYSIS

(71) Applicant: Nanyang Technological University, Singapore (SG)

(72) Inventors: Kijoon Lee, Singapore (SG); Renzhe Bi, Singapore (SG); Jing Dong, Singapore (SG)

(73) Assignee: Pedra Technology PTE LTD

( * ) Notice: Subject to any disclaimer, the term of this patent is extended or adjusted under 35 U.S.C. 154(b) by 0 days.

(21) Appl. No.: 14/155,015

(22) Filed: Jan. 14, 2014

(65) Prior Publication Data

US 2014/0206980 A1 Jul. 24, 2014

Related U.S. Application Data

(60) Provisional application No. 61/755,700, filed on Jan. 23, 2013, provisional application No. 61/830,256, filed on Jun. 3, 2013.

(51) Int. Cl.
*A61B 5/026* (2006.01)
*A61B 5/00* (2006.01)

(52) U.S. Cl.
CPC .......... *A61B 5/0261* (2013.01); *A61B 5/7246* (2013.01)

(58) Field of Classification Search
CPC .................................................. A61B 5/0261
See application file for complete search history.

(56) References Cited

U.S. PATENT DOCUMENTS

| 4,050,450 A | 9/1977 | Polanyi et al. |
| 5,991,697 A | 11/1999 | Nelson et al. |
| 6,076,010 A | 6/2000 | Boas et al. |
| 6,388,240 B2 | 5/2002 | Schulz et al. |

(Continued)

FOREIGN PATENT DOCUMENTS

| AU | 2014209741 | 11/2018 |
| CN | 101404929 | 4/2009 |

(Continued)

OTHER PUBLICATIONS

Bi et al., "Multi-channel deep tissue flowmetry based on temporal diffuse speckle contrast analysis," *Opt Express*, Sep. 23, 2013;21(19):22854-61 (8 pages).

(Continued)

*Primary Examiner* — Rochelle D Turchen
(74) *Attorney, Agent, or Firm* — Knobbe Martens Olson & Bear, LLP

(57) ABSTRACT

Blood flow rates can be calculated using diffuse speckle contrast analysis in spatial and time domains. In the spatial domain analysis, a multi-pixel image sensor can be used to detect a spatial distribution of speckles in a sample caused by diffusion of light from a coherent light source that is blurred due to the movement of scatterers within the sample (e.g., red blood cells moving within a tissue sample). Statistical analysis of the spatial distribution can be used to calculate blood flow. In the time domain analysis, a slow counter can be used to obtain time-series fluctuations in light intensity in a sample caused by diffusion of light in the sample that is smoothened due to the movement of scatterers. Statistical analysis of the time-series data can be used to calculate blood flow.

16 Claims, 9 Drawing Sheets

(56) References Cited

U.S. PATENT DOCUMENTS

| | | | |
|---|---|---|---|
| 6,546,267 B1 | 4/2003 | Sugiura et al. | |
| 6,549,284 B1 | 4/2003 | Boas et al. | |
| 7,043,287 B1 | 5/2006 | Khalil et al. | |
| 7,113,817 B1 | 9/2006 | Winchester, Jr. et al. | |
| 7,460,900 B1 | 12/2008 | Gill et al. | |
| 8,082,015 B2 | 12/2011 | Yodh et al. | |
| 8,480,579 B2 | 7/2013 | Serov et al. | |
| 8,666,468 B1 | 3/2014 | Al-Ali | |
| 8,965,473 B2 | 2/2015 | Hoarau et al. | |
| 9,636,025 B2 | 5/2017 | Lee et al. | |
| 10,213,122 B2 | 2/2019 | Lee et al. | |
| 2002/0180972 A1 | 12/2002 | Ansari et al. | |
| 2004/0243006 A1 | 12/2004 | Nakata et al. | |
| 2006/0063995 A1 | 3/2006 | Yodh et al. | |
| 2007/0179366 A1 | 8/2007 | Pewzner et al. | |
| 2007/0208404 A1* | 9/2007 | Jones | A61N 1/36021 607/148 |
| 2008/0082135 A1 | 4/2008 | Arcot-Krishnamurthy et al. | |
| 2008/0287808 A1 | 11/2008 | Tearney et al. | |
| 2009/0091741 A1* | 4/2009 | Dogariu | G01N 33/4905 356/39 |
| 2009/0149764 A1 | 6/2009 | Semler et al. | |
| 2009/0177107 A1 | 7/2009 | Guion-Johnson | |
| 2009/0287076 A1 | 11/2009 | Boyden et al. | |
| 2010/0016733 A1 | 1/2010 | Smith et al. | |
| 2010/0056928 A1 | 3/2010 | Zuzak et al. | |
| 2010/0210931 A1 | 8/2010 | Cuccia et al. | |
| 2011/0013002 A1 | 1/2011 | Thompson et al. | |
| 2011/0028854 A1 | 2/2011 | Addison et al. | |
| 2011/0128555 A1* | 6/2011 | Rotschild | G02B 27/2271 356/625 |
| 2012/0071769 A1 | 3/2012 | Dunn et al. | |
| 2012/0095354 A1 | 4/2012 | Dunn et al. | |
| 2012/0130215 A1 | 5/2012 | Fine et al. | |
| 2012/0184831 A1 | 7/2012 | Seetamraju et al. | |
| 2012/0188354 A1* | 7/2012 | Munro | H04N 5/332 348/77 |
| 2012/0245439 A1 | 9/2012 | Andre et al. | |
| 2014/0052006 A1 | 2/2014 | Lee et al. | |
| 2014/0094666 A1* | 4/2014 | Fine | A61B 5/7246 600/316 |
| 2014/0111671 A1* | 4/2014 | Cao et al. | 348/241 |
| 2015/0073271 A1 | 3/2015 | Lee et al. | |
| 2016/0007865 A1 | 1/2016 | Sakata et al. | |
| 2017/0231510 A1 | 8/2017 | Lee et al. | |
| 2017/0311819 A1 | 11/2017 | Lee et al. | |
| 2018/0368705 A1 | 12/2018 | Lee et al. | |
| 2020/0022595 A1 | 1/2020 | Lee et al. | |
| 2020/0093382 A1 | 3/2020 | Lee et al. | |
| 2021/0030283 A1 | 2/2021 | Looi et al. | |

FOREIGN PATENT DOCUMENTS

| | | |
|---|---|---|
| CN | 105188523 A | 12/2015 |
| CN | 105451640 A | 3/2016 |
| CN | 107661107 A | 2/2018 |
| CN | 110680287 A | 1/2020 |
| CN | 105636512 A | 11/2020 |
| EP | 3003126 | 4/2016 |
| EP | 2948052 A4 | 6/2016 |
| EP | 3033005 | 6/2016 |
| IN | 201617007572 | 7/2016 |
| JP | 34-34325 | 2/1989 |
| JP | 2001-112717 | 4/2001 |
| JP | 2002-248104 | 9/2002 |
| JP | 2008/237775 | 10/2006 |
| JP | 2008/154804 | 7/2008 |
| JP | 2009-526590 | 7/2009 |
| JP | 6438463 | 11/2018 |
| JP | 6810833 | 12/2020 |
| KR | 20040001568 | 1/2004 |
| KR | 10-2008-0110752 | 12/2008 |
| MX | 369421 | 10/2019 |
| MX | 372511 | 5/2020 |
| WO | WO 97/43950 | 11/1997 |
| WO | WO 2007/017661 A1 | 2/2007 |
| WO | WO 2008/033909 | 3/2008 |
| WO | WO 2011/070357 | 6/2011 |
| WO | WO 2012/065140 A2 | 5/2012 |
| WO | WO 2018/209090 A1 | 11/2018 |
| WO | WO 2020/183401 | 9/2020 |

OTHER PUBLICATIONS

Bi et al., "Deep tissue flowmetry based on diffuse speckle contrast analysis," Opt Lett. May 1, 2013;38(9):1401-3 (3 pages).

Dong et al., "Diffuse correlation spectroscopy with a fast Fourier transform-based software autocorrelator," J Biomed Opt. Sep. 2012;17(9) (10 pages).

PCT Search Report and Written Opinion dated May 13, 2014 in App. No. PCT/US2014/011675 in 5 pages.

Boas, David A., and Andrew K. Dunn. "Laser speckle contrast imaging in biomedical optics." Journal of biomedical optics 15.1 (2010): 011109-011109.

Briers, J. David, and Sian Webster. "Laser speckle contrast analysis (LASCA): a nonscanning, full-field technique for monitoring capillary blood flow." Journal of biomedical optics 1.2 (1996): 174-179.

Chin, Lee CL, William M. Whelan, and I. Alex Vitkin. "Optical fiber sensors for biomedical applications." Optical-Thermal Response of Laser-Irradiated Tissue. Springer Netherlands, 2011. 661-712.

Final Office Action in U.S. Appl. No. 13/967,298 dated Sep. 30, 2015 in 25 pages.

Forrester, Kevin R., et al. "A laser speckle imaging technique for measuring tissue perfusion." Biomedical Engineering, IEEE Transactions on 51.11 (2004): 2074-2084.

Huang, Yu-Chih, et al. "Noninvasive blood flow imaging for real-time feedback during laser therapy of port wine stain birthmarks." Lasers in surgery and medicine 40.3 (2008): 167-173.

Dunn, Andrew K. "Laser speckle contrast imaging of cerebral blood flow." Annals of biomedical engineering 40.2 (2012): 367-377.

Notice of Allowance dated Dec. 19, 2016 in U.S. Appl. No. 13/967,298 in 9 pages.

Sigal, Iliya, et al. "Laser speckle contrast imaging with extended depth of field for in-vivo tissue imaging." Biomedical optics express 5.1 (2014): 123-135.

European Search Report and Opinion in EP. App. No. 14743829.5 dated Aug. 22, 2016 in 5 pages.

Armitage, Glenn A., et al. "Laser speckle contrast imaging of collateral blood flow during acute ischemic stroke." Journal of Cerebral Blood Flow & Metabolism 30.8 (2010): 1432-1436.

Basak, Kausik, M. Manjunatha, and Pranab Kumar Dutta. "Review of laser speckle-based analysis in medical imaging." Medical & biological engineering & computing 50.6 (2012): 547-558.

Berndt, Kersten, et al. "A new method for repeated drug infusion into the femoral artery of mice." Journal of the American Association for Laboratory Animal Science 51.6 (2012): 825-831.

Binzoni, T., et al. "Non-invasive laser Doppler perfusion measurements of large tissue volumes and human skeletal muscle blood RMS velocity." Physics in medicine and biology 48.15 (2003): 2527.

Bizheva, Kostadinka K., Andy M. Siegel, and David A. Boas. "Path-length-resolved dynamic light scattering in highly scattering random media: The transition to diffusing wave spectroscopy." Physical Review E 58.6 (1998): 7664.

Briers, David, et al. "Laser speckle contrast imaging: theoretical and practical limitations." Journal of biomedical optics 18.6 (2013): 066018-066018.

Cheng, Haiying, et al. "Modified laser speckle imaging method with improved spatial resolution." Journal of Biomedical Optics 8.3 (2003): 559-564.

Cheng, Haiying, Yumei Yan, and Timothy Q. Duong. "Temporal statistical analysis of laser speckle images and its application to retinal blood-flow imaging." Optics express 16.14 (2008): 10214-10219.

(56) References Cited

OTHER PUBLICATIONS

Davis, Mitchell A., SM Shams Kazmi, and Andrew K. Dunn. "Imaging depth and multiple scattering in laser speckle contrast imaging." Journal of biomedical optics 19.8 (2014): 086001-086001.
Mahé, Guillaume, et al. "Assessment of skin microvascular function and dysfunction with laser speckle contrast imaging." Circulation: Cardiovascular Imaging 5.1 (2012): 155-163.
Miao, Peng, et al. "Laser speckle contrast imaging of cerebral blood flow in freely moving animals." Journal of biomedical optics 16.9 (2011): 090502-090502.
O'Doherty, Jim, et al. "Comparison of instruments for investigation of microcirculatory blood flow and red blood cell concentration." Journal of biomedical optics 14.3 (2009): 034025-034025.
Ramirez, J. et al. "Impact of velocity distribution assumption on simplified laser speckle imaging equation." Optics Express, Mar. 3, 2008 vol. 16 No. 5: 3197-3203.
Sandell et al., "A review of in-vivo optical properties of human tissues and its impact on PDT." J. Biophotonics Nov. 2011; 4(11-12) 773-787.
Yu et al. "Near-infrared diffuse correlation spectroscopy for assessment of tissue blood flow." Handbook of Biomedical Optics. CRC Press, 2011. 195-216.
Zhang, Xiangdong, and Zhao-Qing Zhang. "Wave transport through thin slabs of random media with internal reflection: Ballistic to diffusive transition." Physical Review E 66.1 (2002): 016612.
Office Action in U.S. Appl. No. 13/967,298 dated May 4, 2016 in 13 pages.
The Basics of Fiber Optic Cable available at https://arcelect.com/fibercable.htm in 12 pages, accessed Feb. 27, 2018.
Castronuovo, Jr. MD. et al., "Skin perfusion pressure measurement is valuable in the diagnosis of critical limb ischemia" Journal of Vascular Surgery, Oct. 1997.
Chen et al., "Blood Flow Dynamics after Photodynamic Therapy with Verteporfin in the RIF-1 Tumor," Radiation Research vol. 160, pp. 452-459, 2003.
Cheng, et al. "Laser speckle imaging blood flow in microcirculation." Physics in medicine and Biology, Institute of Physics Publishing, Bristol GB, vol. 49, No. 7, Apr. 7, 2004 (Apr. 7, 2004), pp. 1347-1357, XP020024077, ISSN: 0031-9155, DOI: 10.1088/0031-9155/49/7/020.
Ebihara, Akira, et al. "Detection of cerebral ischemia using the power spectrum of the pulse wave measured by near-infrared spectroscopy." Journal of biomedical optics 18.10 (2013): 106001-1-106001-8.
Extended Search Report in European Application No. 13886377.4 dated Feb. 17, 2017 in 8 pages.
European Search Report in EP patent application No. 14836211.4 dated Feb. 3, 2017 in 6 pages.
Fife et al., "The predictive value of transcutaneous oxygen tension measurement in diabetic lower extremity ulcers treated with hyperbaric oxygen therapy: a retrospective analysis of 1144 patients," Wound Repair and Regeneration vol. 10, No. 4, pp. 198-207, 2002.
Figoni et al., "Preamputation evaluation of limb perfusion with laser Doppler imaging and transcutaneous gases," Journal of Rehabilitation research & Development, vol. 43, No. 7, pp. 891-904, Nov./Dec. 2006.
Fourier transform by Wikipedia; published onlin on Aug. 9, 2013 at https://en.wikipedia.org/w/index.php?title=Fourier_transform&oldid=567869073>.
He, Heng et al., "Lateral laser speckle Contrast Analysis combined with Line Beam scanning Illumincation to improve the Sampling Depth of Blood Flow Imaging," Optics Letters/vol. 37, No. 18, Sep. 15, 2012, pp. 3774-3776.
Huang, Han-Wei, et al. "Power spectral analyses of index finger skin blood perfusion in carpal tunnel syndrome and diabetic polyneuropathy." Experimental diabetes research 2011 (2011).
International Search Report and Written Opinion for PCT/US2014/011675, dated May 13, 2014 (12 pages).
International Search Report for International Application No. PCT/IB2014/002521 dated May 22, 2015 in 5 pages.
International Search Report for International Application No. PCT/IB2020/052173 dated Jun. 5, 2020 in 10 pages.
Jordan, M.S. et al., "Nitric Oxide-Mediated Increase in Tumor Blood Flow and Oxygenation of Tumors Implanted in Muscles Stimulated by Electric Pulses," International Journal of Radiation Oncology Biol. Phys. vol. 55, No. 4, pp. 1066-1073, 2003.
Kolluru et al., "Endothelial Dysfunction and Diabetes: Effects on Angiogenesis, Vascular Remodeling, and Wound Healing," International Journal of Vascular Medicine, vol. 2012, 30 pages, 2012.
Kvandal et al., "Low -frequency oscillations of the laser Doppler perfusion signal in human skin," Microvascular Research 72 (2006) 120-127.
Langen et al., "Use of H2 15O-PET and DCE-MRI to Measure Tumor Blood Flow," The Oncologist Cancer Imaging, vol. 13, pp. 631-644, 2008.
Lin, Yu et al., "Noncontact diffuse correlation spectroscopy for noninvasive deep tissue blood flow measurement," Journal of Biomedical Optics, vol. 17, No. 1, Jan. 2012.
Lo et al., "Prediction of Wound Healing Outcome Using Skin Perfusion Pressure and Transcutaneous Oximetry: A Single-Center Experience in 100 Patients," Wounds, vol. 21, No. 11, pp. 310-316, 2009.
Plafki, M.D., et al., "Complications and Side Effects of Hyperbaric Oxygen Therapy," Aviation, Space, and Environmental Med. vol. 71, No. 2, pp. 119-124, Feb. 2000.
Rossi, Marco, et al. "Spectral analysis of laser Doppler skin blood flow oscillations in human essential arterial hypertension." Microvascular research 72.1 (2006): 34-41.
Rücker et al., "Vasomotion in critically perfused muscle protects adjacent tissues from capillary perfusion failure," Am. J. Physiol. Heart Circ. Physiol., vol. 279, H550-H558, 2000.
Schmidt, MD, et al., "Periodic hemodynamics (flow motion) in peripheral arterial occlusive disease," Journal of Vascular Surgery, vol. 18, pp. 207-215, Aug. 1993.
Stansberry, BS et al., "Impaired Peripheral Vasomotion in Diabetes," Diabetes Care, vol. 19, No. 7, pp. 715-721, Jul. 1996.
Supplementary European Search Report in European application No. 14743829.5 dated Aug. 22, 2016.
Suzuki et al., "Lower Extremity Peripheral Arterial Disease: Diagnosis and Treatment Update 2012" Podiatry Today, vol. 25, No. 7, pp. 84-92, 2012.
Wavelet transform by Wikipedia; published online on Aug. 6, 2013 at https://en.wikipedia.org/w/index.php?title=Wavelet_transform&oldid=567370052>.
Yu, G., Diffuse Correlation Spectroscopy (DCS): A Diagnostic Tool for Assessing Tissue Blood Flow in Vascular-Related Diseases and Therapies, Current Medical Imaging Reviews, vol. 8, No. 3, 2012, pp. 194-210.
Yu, G. et al., "Time-Dependant blood flow and oxygenation in human skeletal muscles measured with noninvasive near-infrared diffuse optical spectroscopies," Journal of Biomedical Optics, vol. 10, No. 2, Mar./Apr. 2005.
Zimnyakov D.A. et al., "Full-field speckle Techniques in Blood Microcirculation Monitoring," Visual Communications and Image Processing; vol. 4241, Oct. 3, 2000, pp. 370-377.

\* cited by examiner

DEEP TISSUE FLOWMETRY USING DIFFUSE SPECKLE CONTRAST ANALYSIS

CROSS-REFERENCE TO RELATED APPLICATIONS

This application claims the benefit of priority to U.S. Provisional App. No. 61/755,700, filed on Jan. 23, 2013, and to U.S. Provisional App. No. 61/830,256, filed Jun. 3, 2013. The entire contents of each of these applications are hereby incorporated by reference.

BACKGROUND

Field of the Invention

This disclosure relates to systems and methods for measuring deep tissue flow, particularly via non-invasive optical approaches.

Description of the Related Art

Diffuse correlation spectroscopy (DCS), a noninvasive optical method to probe deep tissue flow. The principle of DCS is based on the fact that transmitted light intensity measured at a sufficiently small area will fluctuate primarily due to the movement of the scatterers (such as red blood cells) in the course of the diffuse light propagation. Therefore, when the autocorrelation function is calculated from the fluctuating transmission light intensity, the decay rate of the autocorrelation will be proportionally higher as flow rate increases.

Although successful in monitoring averaged microcirculation in deep tissue, DCS suffers from several disadvantages, including sophisticated hardware requirements (for example, long coherence length laser, photon-counting avalanche photodiode, fast counter, etc.), non-trivial data analysis (for example, fast autocorrelation calculation, model fit by optimization, etc.), low sampling rate, and low channel number, rendering multichannel measurements difficult. These limitations pose challenges for the application of DCS as a stable, real-time clinical monitoring device. Accordingly, there is a need for an improved method for noninvasive, real-time measurement of blood perfusion with reduced computational complexity, decreased expense, a high sampling rate, and multichannel capabilities.

SUMMARY OF THE INVENTION

Disclosed herein is a method for determining blood flow in a patient, the method comprising: directing coherent light onto a first location of the patient's skin; imaging a second location of the patient's skin, wherein a portion of the coherent light is scattered by the blood flow beneath the patient's skin such that the scattered light is at least partially detectable at the second location; and calculating the blood flow based on the image of the second location.

In some embodiments, the calculation can comprise calculating the speckle contrast. In some embodiments, calculating the speckle contrast comprises dividing the standard deviation of intensity by the average intensity of the image of the second location. In some embodiments, the blood flow can be at least 5 mm below the surface of the patient's skin. In some embodiments, the first and second locations can be on a patient's limb. In some embodiments, the first and second locations can be on a patient's foot. In some embodiments, imaging the second location can comprise capturing an image with a multi-pixel image sensor. In some embodiments, the coherent light can comprise light from a laser. In some embodiments, the first and second locations can be at least 10 mm apart. In some embodiments, the method can further comprise signaling the blood flow to an operator.

Also disclosed herein is a method for determining blood flow in a patient, the method comprising: directing coherent light onto a first location of the patient's skin; detecting time-series measurements of the light intensity at a second location of the patient's skin, wherein a portion of the coherent light is scattered by the blood flow beneath the patient's skin such that the scattered light is at least partially detectable at the second location; and calculating the blood flow based on the time-series measurements.

In some embodiments, the calculating can comprise calculating the spatial and temporal contrast. In some embodiments, calculating the temporal speckle contrast can comprise dividing the temporal standard deviation of intensity by the temporal average intensity at the second location. In some embodiments, the blood flow can be at least 5 mm below the surface of the patient's skin. In some embodiments, the first and second locations can be on a patient's foot. In some embodiments, the first and second locations can be less than 10 mm apart. In some embodiments, the first and second locations can be at least 10 mm apart. In some embodiments, the method can further comprise signaling the blood flow an operator. In some embodiments, the signaling can comprise providing audible, visual, or tactile indicia of blood flow.

Further disclosed herein is a system for assessment of blood flow in tissue, the system comprising: a coherent light source configured to apply light to the tissue; a multi-pixel image sensor detector configured to capture an image including at least a quantity of light transmitted through the tissue, wherein the light is scattered, at least in part, by the blood flow; an analyzer configured to analyze the image to determine blood flow in the tissue; and a feedback device configured to provide a signal indicative of the blood flow determined by the analyzer.

In some embodiments, the multi-pixel image sensor can comprise a CCD camera. In some embodiments, the analyzer can be configured to calculate the spatial speckle contrast by dividing the standard deviation of intensity by the average intensity. In some embodiments, the system can be configured to provide the signal indicative of the blood flow in substantially real-time.

DETAILED DESCRIPTION OF THE PREFERRED EMBODIMENT

Over the last decade or so, DCS technology has been developed, validated, and employed to noninvasively probe the blood flow information in deep tissue vasculature such as brain, muscle, and breast. In contrast to some other blood flow measurement techniques, such as positron emission tomography (PET), single photon emission computed tomography (SPECT), and xenon-enhanced computed tomography (XeCT), DCS uses non-ionizing radiation and requires no contrast agents. It does not interfere with commonly used medical devices such as pacemakers and metal implants. It therefore has potential in cancer therapy monitoring and bedside monitoring in clinical settings.

However, traditional DCS analysis suffers from a long integration time, high cost, and low channel number of simultaneous measurements. One factor contributing to these limitations is dependence on very sensitive photodetector and subsequent autocorrelation calculation. An improved flowmetry system provides cost-effective, real-time measurements using statistical analysis without having to rely on autocorrelation analysis on fast time-series data. This statistical analysis can be implemented either in spatial domain using a multi-pixel image sensor, or in the time domain using slow counter. A multi-pixel image sensor can also be used for time domain analysis such that single or multiple pixels act as an individual detector, which is especially suitable for multi-channel application. In various embodiments, this approach can be used to measure blood flow, either absolute, relative, or both.

Figure 1:
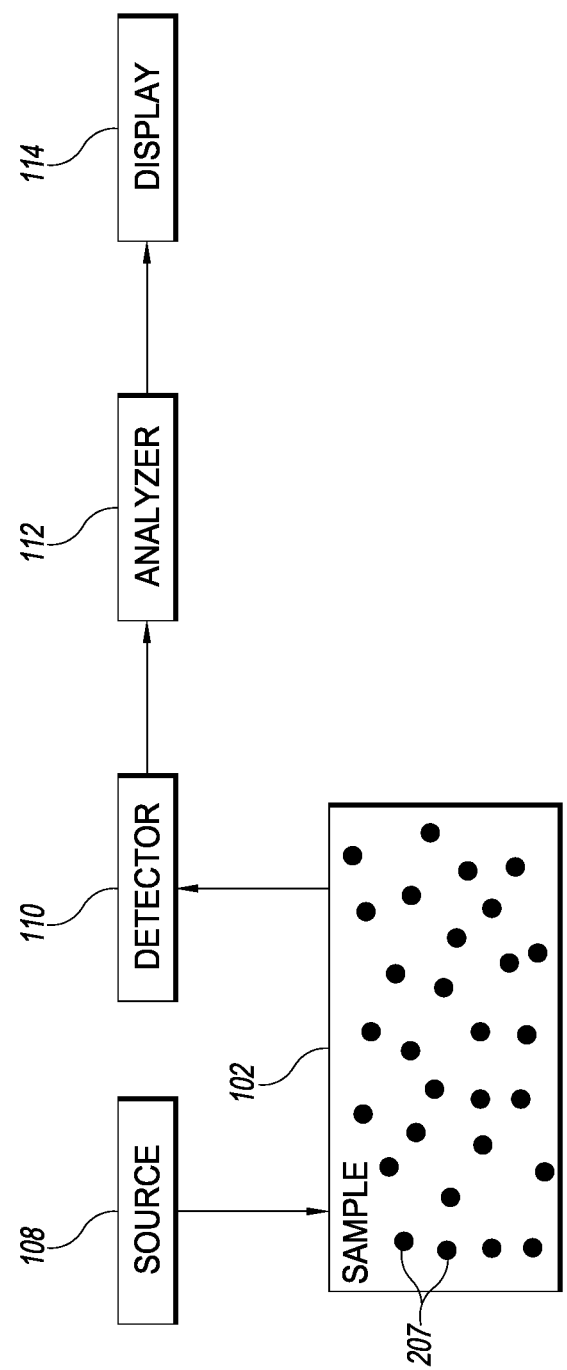
FIG. 1 is a block diagram of a system for measuring flow of turbid media.

FIG. 1 is a block diagram of a system for measuring flow of turbid media. A sample 102 includes a heterogeneous matrix therein. Within this matrix is an embedded flow layer with randomly ordered microcirculatory channels through which small particles 207 move in a non-ordered fashion. For example, in some embodiments the sample may be body tissue, with a complex network of peripheral arterioles and capillaries. A source 108 injects light into the sample 102. A detector 110 can detect light scattered by the moving particles 207 in the microcirculatory channels. The detector 110 can be positioned to receive light that passes from the source into the sample, and diffuses through the sample. In some embodiments, the detector can be coupled to the sample by a single-mode optical fiber. In some embodiments, the detector may be a multi-pixel image sensor, for example a CCD camera, used to image an area of the sample. In other embodiments, the detector may be a photon-counting avalanche photodiode (APD) or photomultiplier tube (PMT). As the particles flow in random directions, the scattering of light from the source 108 will vary, causing intensity fluctuations to be detected by the detector 110.

An analyzer 112 is coupled to detector 110 and configured to receive a signal from the detector 110. The time-dependent intensity fluctuations reflect the time-dependent displacements of particles 207 within the sample 102, and accordingly the signal from the detector 110 may be used to determine the flow rate of the particles 207 within the sample 102.

The flow rate or other characteristic determined by the analyzer 112 may be output to a display 114. The measured quantity may therefore be provided to an operator via the display 114. In various embodiments, the operator may be a clinician, diagnostician, surgeon, surgical assistant, nurse, or other medical personnel. In some embodiments, the measurement may be provided via display 114 in substantially real-time. In some embodiments, the measurement may be provided via display 114 within about 1 second from measurement, i.e., within about 1 second of the time that the scattered light is detected by the detector, the measurement may be provided via display 114. In various embodiments, the measurement may be provided within less than about 10 minutes, within less than about 5 minutes, within less than about 1 minute, within less than about 30 seconds, within less than about 10 seconds, or within less than about 1 second from measurement.

Figure 2:
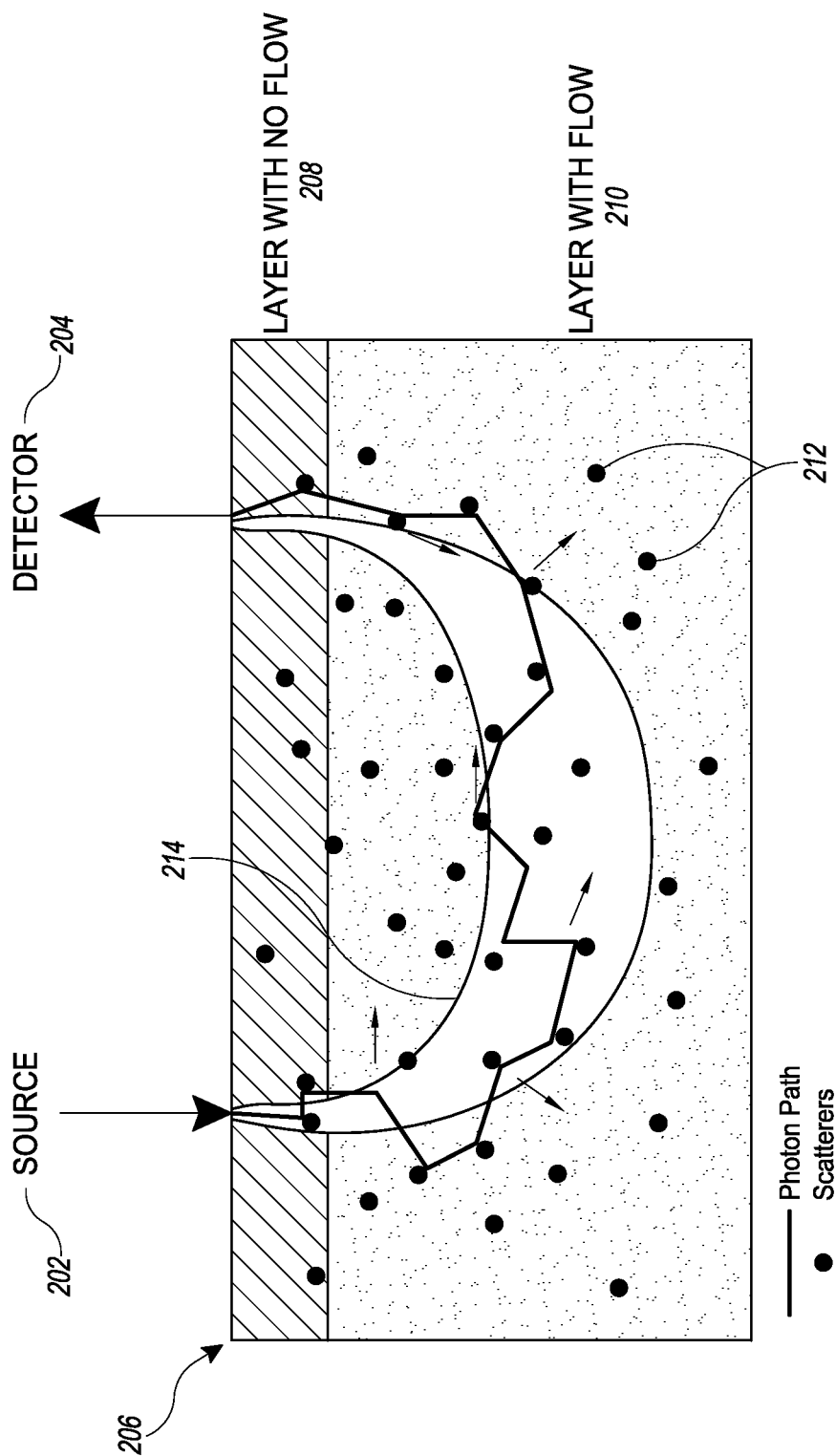
FIG. 2 is a schematic illustration of diffuse light penetration and detection in multi-layer tissue.

FIG. 2 is a schematic illustration of diffuse light penetration and detection in multi-layer tissue. As illustrated, a source 202 and a detector 204 are both positioned adjacent a portion of tissue 206. As noted above, in some embodiments optical fibers may be used to couple one or both of the source and detector to the tissue. The tissue 206 is multi-layer, including an upper layer 208 with no flow, and a deeper layer 210 with flow. A plurality of light-scattering particles 212 flow within capillaries in flow layer 210, and may include, for example, red blood cells. As light 214 is emitted from the source 202, it diffuses as it penetrates the tissue 206. As illustrated, a portion of the light 214 is diffused such that it is incident on the detector 204. The light 214 may follow a roughly crescent-shaped path from the source 202 to the detector 204. The depth of penetration of the light 214 detected by the detector 204 depends on the separation between the source and the detector. As the distance increases, penetration depth generally increases. In various embodiments, the separation distance may be between about 0.5 cm and about 10 cm, or in some embodiments between about 0.75 cm and about 5 cm. Preferably, in other embodiments the separation distance may be between about 1 cm and about 3 cm. In various embodiments, the separation distance may be less than about 10 cm, less than about 9 cm, less than about 8 cm, less than about 7 cm, less than about 6 cm, less than about 5 cm, less than about 4 cm, less than about 3 cm, less than about 2 cm, less than about 1 cm, less than about 0.9 cm, less than about 0.8 cm, less than about 0.7 cm, less than about 0.5 cm, less than about 0.4 cm, less than about 0.3 cm, less than about 0.2 cm, or less than about 0.1 cm. The penetration depth may vary, for example in some embodiments the penetration depth of the sensor may be between about 0.5 cm and about 5 cm, or in some embodiments between about 0.75 cm and about 3 cm. Preferably, in other embodiments the penetration depth may be between about 5 mm and about 1.5 cm. Of course, the tissue optical properties of the various layers also contribute to the penetration depth of the light, as does the intensity, wavelength, or other characteristics of the light source. These variations can allow for the depth of measurement to be adjusted based on the part of the body being analyzed, the particular patient, or other considerations.

Figure 3B:
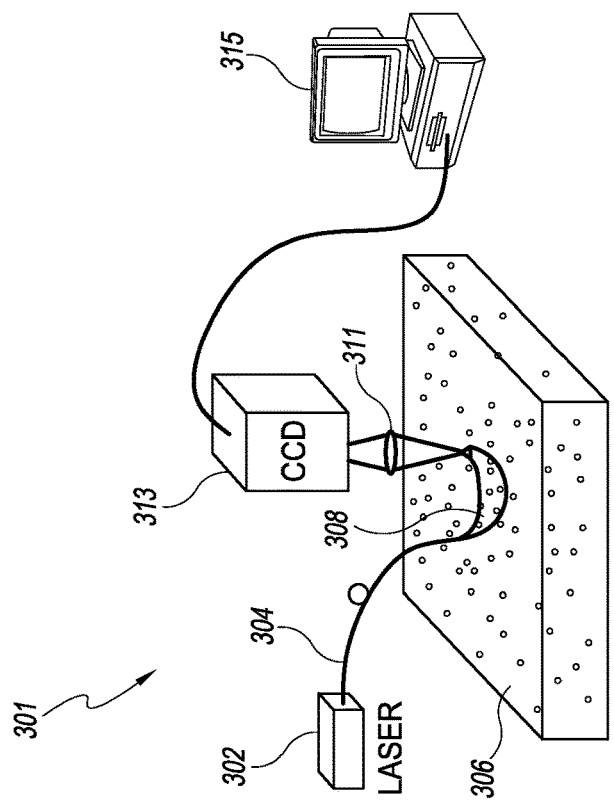
FIG. 3B is a schematic illustration of a diffuse speckle contrast analysis (DSCA) system.
Figure 3A:
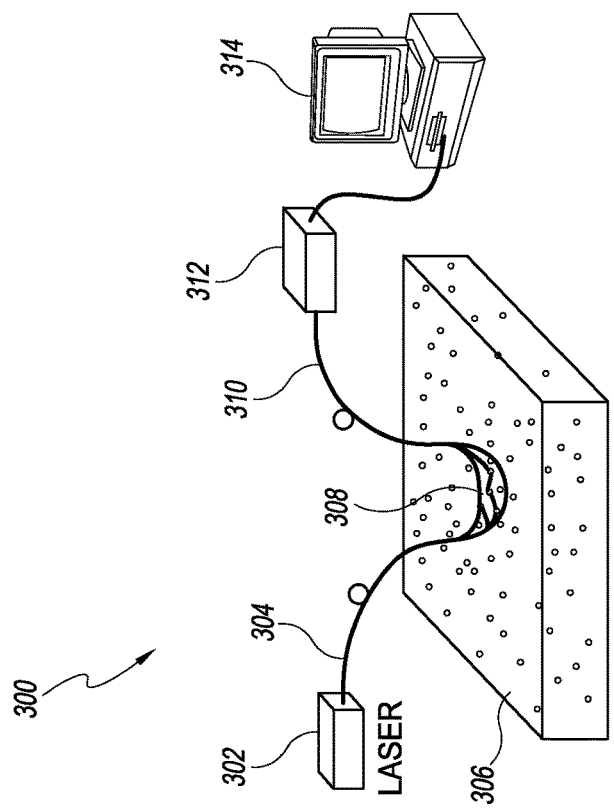
FIG. 3A is a schematic illustration of a diffuse correlation spectroscopy (DCS) system.

FIG. 3A is a schematic illustration of a diffuse correlation spectroscopy (DCS) system 300. As illustrated, a laser 302 directs light via an input optical fiber 304 into a sample 306. Moving particles are distributed within the sample. The incident light 308 diffuses through the sample 306, affected by the movement of the particles, and is detected via output optical fiber 310 by detector 312. In a DCS system, the detector can be, for example, a photon-counting avalanche photodiode (APD) or photomultiplier tube (PMT). An analyzer 314 is configured to receive a signal from the detector 312. For the DCS system, the analyzer 112 includes an autocorrelator, which calculates the temporal intensity autocorrelation function of light received by the detector 312. The autocorrelation function can be used to obtain the scattering and flow characteristics of the small particles in the sample 304. The time-dependent intensity fluctuations reflect the time-dependent displacements of the scatterers of the sample 306, and accordingly the autocorrelation function can be used to determine the flow rate within the sample 306. As noted previously, the DCS system requires a precise and fast-counting detector such as an APD or PMT. Additionally, calculating the autocorrelation function is computationally intensive, and the DCS approach favors single-channel measurement.

FIG. 3B is a schematic illustration of a diffuse speckle contrast analysis (DSCA) system. The illustrated system 301 is configured for spatial domain DSCA (sDSCA). As shown, several components are similar to those in the DCS system of FIG. 3A, including laser 302, input optical fiber 304, sample 306 having moving particles therein, and light 308 diffusing through the sample 306 from the input fiber 304. However, in contrast to the output fiber and detector of the DCS system, the sDCSA system 301 uses relay optics 311 and a CCD camera 313. The relay optics 311 are optional, and may, for example, comprise one or more optical fibers, lenses, mirrors, prisms, or other optical elements. This configuration does not require a fast detector and counter, and furthermore allows simultaneous measurements on many detector positions in an area covered by CCD, compared with the single position measurement by the DCS approach. The detector is therefore greatly simplified by use of a CCD camera 313.

As shown in FIG. 3A, traditional DCS makes use of two optical fibers, an input fiber 304 to deliver source light, which is typically a multimode fiber, and an output fiber 310 for detecting fluctuation of the transmitted light on a small region. The output fiber 310 is a singlemode fiber, and the core diameter of the fiber 310 must be comparable to the speckle size to ensure detection of the relevant fluctuating signal. In contrast, the DSCAs system of FIG. 3B utilizes a CCD 313 as a detector. In use, a single image from the CCD camera with an optimized magnification and exposure time may be processed by the analyzer 315 to estimate deep tissue flow. As described in more detail below, the analysis technique in sDSCA differs significantly from that of DCS, providing a number of advantages. For example, as sDSCA does not rely on the computationally intensive autocorrelation calculation, the data analysis is vastly simplified.

Figure 4:
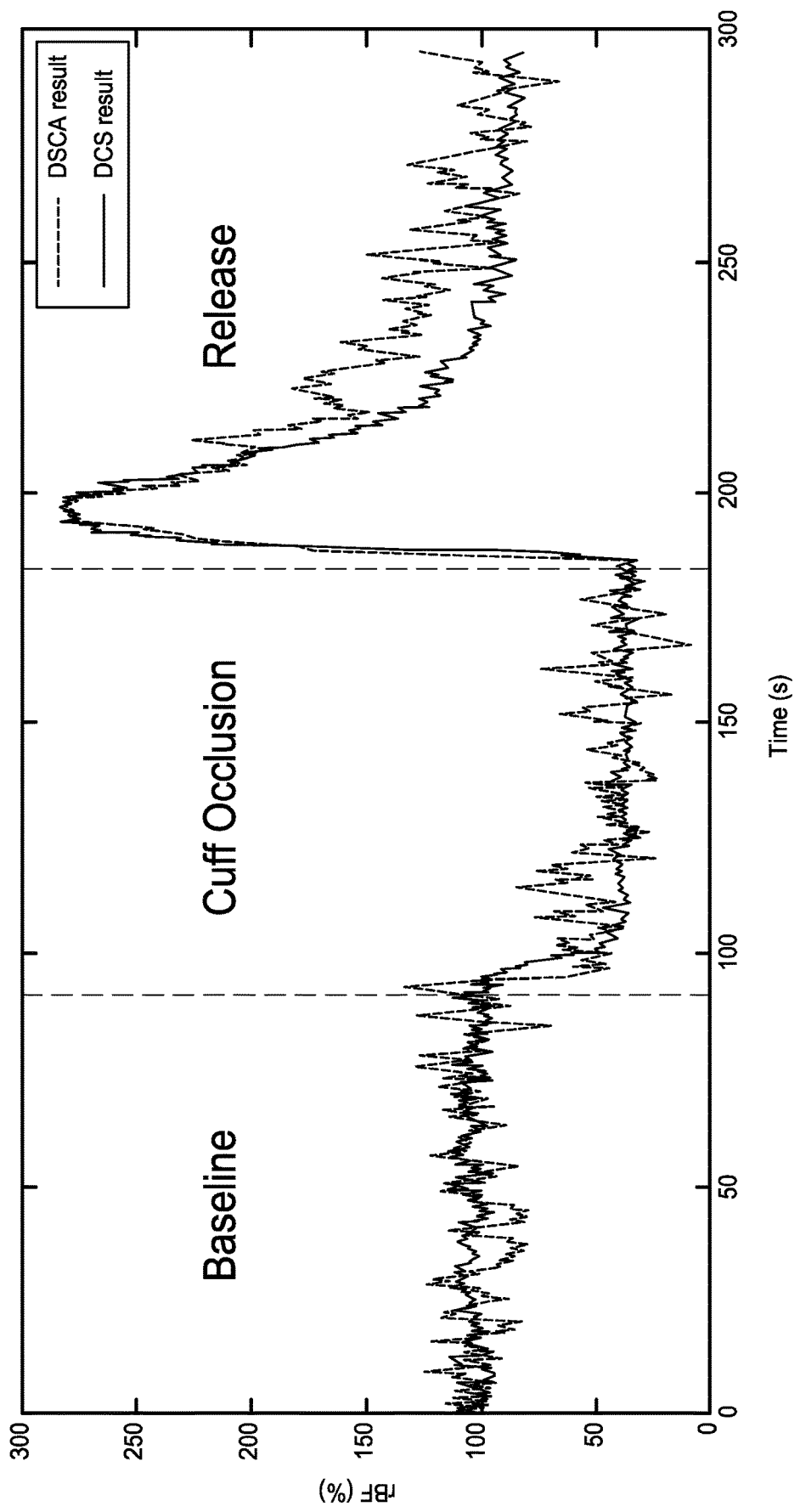
FIG. 4 is a graph of DCS and DSCA measurements of blood flow over time during cuff occlusion protocol.

This simplified instrumentation and data analysis can also provide better time resolution. Since the image processing can be done very quickly, the time resolution is only limited by CCD exposure time and CCD readout time. FIG. 4 illustrates a direct comparison between DSCA and traditional DCS measurement in-vivo using a cuff occlusion protocol. Both show nearly identical trends that reflect physiological activity, including a large decrease of blood flow during cuff occlusion, and reactive hyperemia after releasing the cuff. Moreover, DSCA captures finer time data than DCS, enabling observation of fast physiological changes not possible with conventional DCS, such as the low frequency oscillation of about 0.1 Hz observed by DSCA in FIG. 4. In some embodiments, DSCA can achieve a sampling rate of approximately 30 Hz, compared to the approximately 1 Hz for DCS systems.

Figure 5:
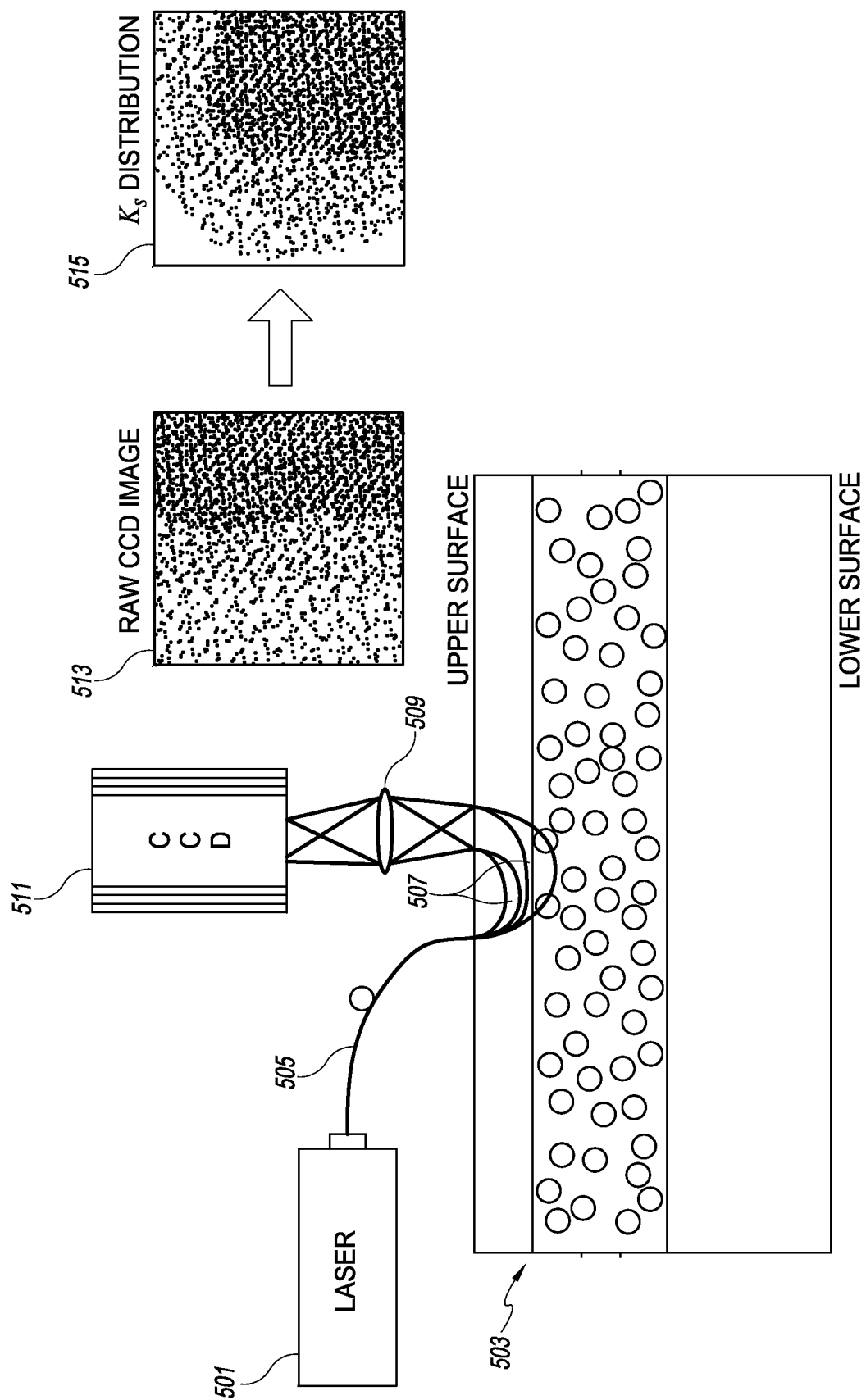
FIG. 5 is a schematic illustration of spatial domain DSCA.

FIG. 5 is a schematic illustration of spatial domain DSCA system. Light from laser 501 is injected into the sample 503 via input optical fiber 505. The laser can provide a long coherence length. The incident light 507 diffuses through the sample 503 and creates a speckle pattern detectable on the upper surface of the sample 503. CCD camera 509 using optional relay optics 511 captures an image of the speckle pattern on the sample 503. Relay optics 511 can include one or more imaging lenses, prisms, mirrors, lens tubes to block stray light, and other optical elements configured to aid the imaging of the speckle pattern on the sample 503 with the CCD camera 509.

Figure 6A:
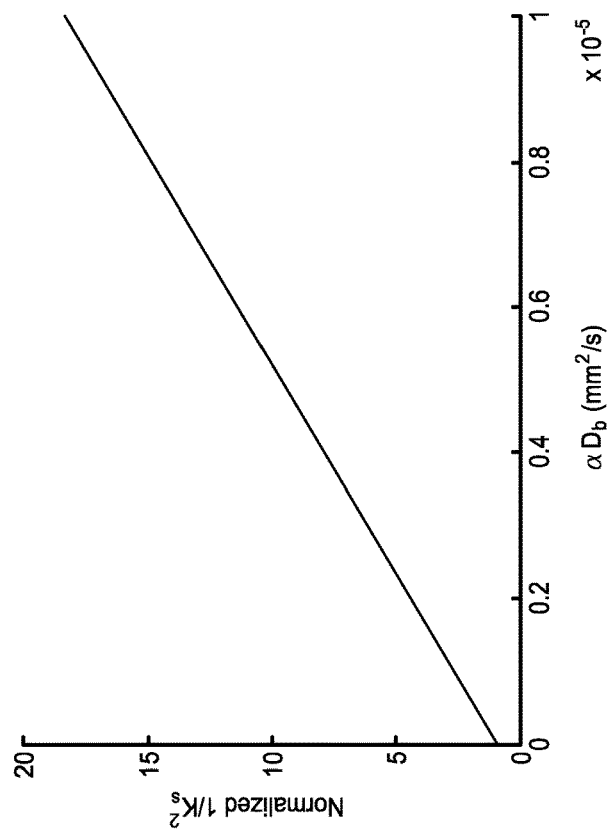
FIG. 6A is a graph of a numerical simulation of $1/K_s^2$ as a function of $\alpha D_b$.
Figure 6B:
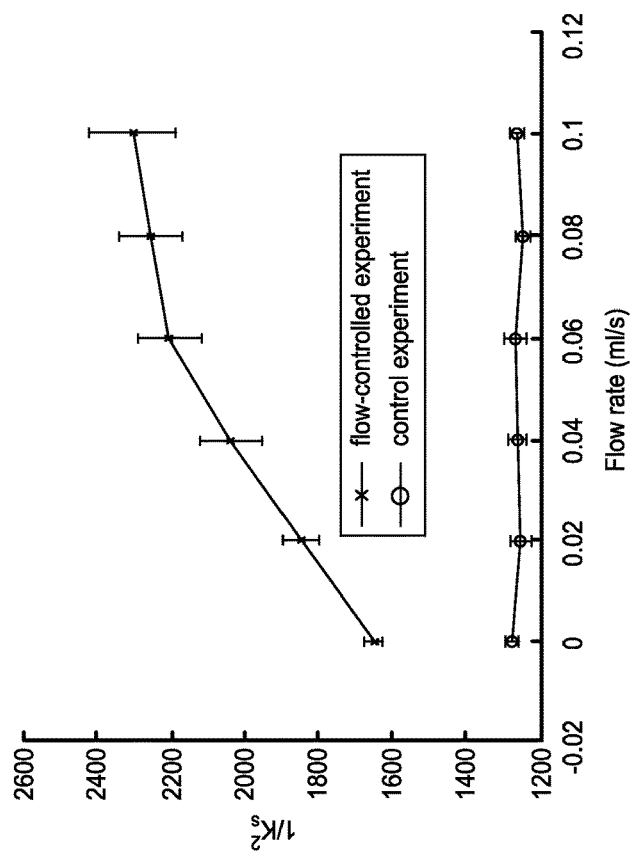
FIG. 6B is a graph of $1/K_s^2$ plotted against measured flow rate.

A representation of the obtained raw CCD image 513 is shown, along with a representation of the calculated $K_s$ distribution 515 where 100×50 pixels were used. The raw speckle image 513 is first obtained from the sample surface. The raw speckle images may first be normalized by the smooth intensity background, which can be averaged over a number of speckle images. The speckle contrast, $K_s$ is defined as the ratio of the standard deviation to the mean intensity across many detectors or pixels, $K_s = \sigma_s/<I>$, where subscript s refers to the spatial, as opposed to temporal, variations. The quantity $K_s$ is related to the field autocorrelation function $g_1(\tau)$ as follows:

$$V(T) = [K_s(T)]^2 = \frac{2}{T}\int_0^T (1-\tau/T)[g_1(\tau)]^2 d\tau$$

where V is the intensity variance across the image, and T is the CCD exposure time. By using the known solution of the correlation diffusion equation in the semi-infinite medium, the formal relationship between the flow rate and $K_s$ can be derived. The relationship between the flow and $1/K_s^2$ turns out to be substantially linear in the range of flow seen in body tissue, with $1/K_s^2$ increasing with increasing flow rate, as is illustrated in FIGS. 6A and 6B. FIG. 6A shows a numerical simulation relating $1/L_s^2$ to the blood flow index ($\alpha D_b$ in a Brownian motion model), while FIG. 6B shows experimental results of the relationship between $1/K_s^2$ to flow rate. Data shown in FIGS. 6B, 6C, and 6D were measured on a flow phantom, shown in FIG. 7. As illustrated in FIG. 7, a phantom 702 includes a flow channel 704, which is between 1 cm and 3.5 cm below the upper surface. A plurality of glass beads 706 is disposed within the flow channel. Intralipid fluid 708 is driven through the flow channel 704 via the peristaltic motor 710. The interstitial spaces between the glass beads 706 within the flow channel 704 simulates microcirculatory flow channels in tissue, and the movement of the intralipid fluid 708 within these interstices simulates arteriole or capillary blood flow. A multimode fiber 712 delivers light into the phantom 702, with a single-mode fiber 714 detecting light scattered by the glass beads 706.

Figures 6C, 6D:
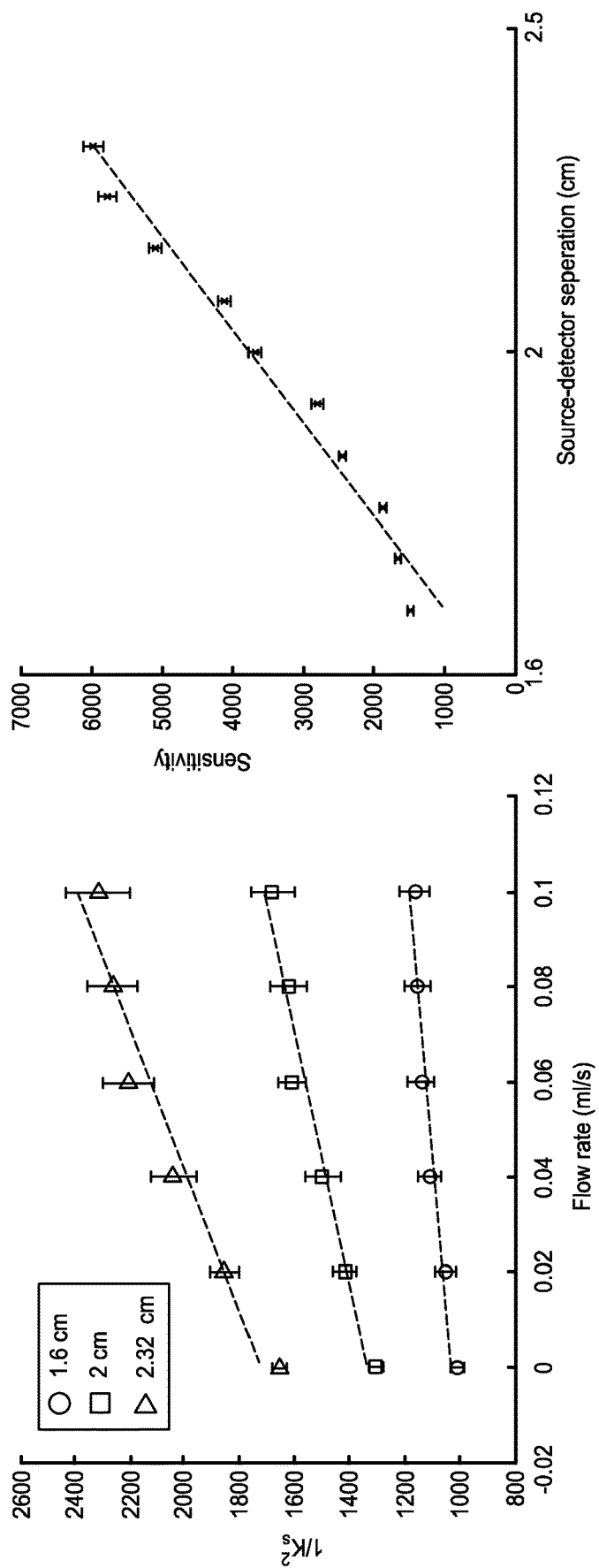
FIG. 6C is a graph of $1/K_s^2$ as a function of the flow rate for three source-detector separation distances.
FIG. 6D is a graph of flow sensitivity for various source-detector separation distances.
Figure 7:
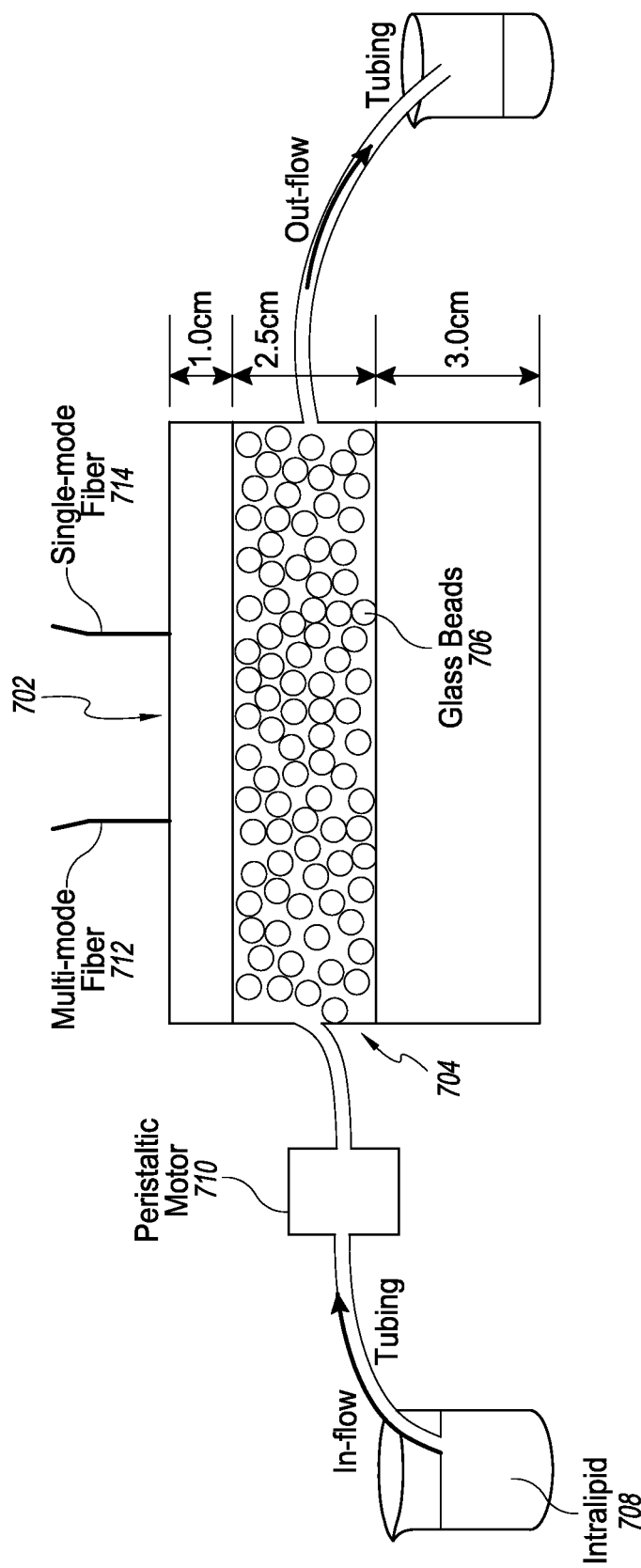
FIG. 7 is a schematic diagram of a phantom flow experiment.

FIG. 6C illustrates the varying linear relationships between $1/K_s^2$ and the flow rate depending on source-detector separation distance when measuring the flow phantom. At smaller source-detector separations, the measurement depth (nominally equal to half the source-detector separation) may not reach the flow channel 704. This accounts for the data associated with a 1.6 cm source-detector separation being largely insensitive to the flow rate within the flow channel 704. As the source-detector separation increases, the measurement depth reaches the flow channel, and the sensitivity of the measurements to the flow rate increases, as reflected in the increased slopes of the data in FIG. 6C.

By dividing the raw image obtained from CCD camera into sub-sections, these sub-sections can each provide different source-detector separation distances. The flow sensitivities calculated from ten source-detector separation distances from a single CCD image are illustrated in FIG. 6D. The use of a single CCD image allows for multi-depth measurements from a single exposure, which may enable a depth-specific measurement of deep tissue blood flow.

Another way to implement this speckle contrast rationale for flowmetry is to use statistical analysis on time series data obtained by integrating over a certain time. This temporal domain analysis is referred to herein as tDSCA. The integrating time for tDSCA can be regarded as analogous to the exposure time of CCD camera in sDSCA. In the case of tDSCA, a detector with moderate sensitivity with an integrating circuit can be used. For example, each pixel on a CCD chip can be used for this purpose as each CCD pixel keeps accumulating photoelectrons for a given exposure time. Therefore, a number of single-mode fibers can be directly positioned on some locations on a single CCD chip, resulting in a multi-channel tDSCA system without losing any time resolution. The number of channels is only limited by the CCD chip size, pixel size, and the area of each fiber tip. In some embodiments, tDSCA can use sensitive detectors such as avalanche photodiode (APD) and/or photomultiplier tube (PMT) with a slow counter such as a counter included in a DAQ card with USB connection, but scaling this embodiment to multichannel instrument is costly and bulky. Time-series data taken either way can be obtained by repeat measurements, for example 25 measurements can be made consecutively, after which the data can be analyzed statistically to determine the flow rate. In a configuration with an exposure time of 1 ms, one flow index would be obtained every 25 ms, resulting in approximately 40 Hz operation.

The statistical analysis of the time-series data can be substantially identical to that described above with respect to sDSCA, except that the statistics (average intensity and standard deviation of intensity) are calculated in the time domain, rather than the spatial domain. As a result, tDSCA may provide lower time resolution than sDSCA. However, the detector area for tDSCA may be significantly smaller than with sDSCA. As with the spatial domain counterpart, tDSCA provides an approach with instrumentation and analysis that are significantly simpler and less computationally intensive than traditional DCS techniques.

Figure 8:
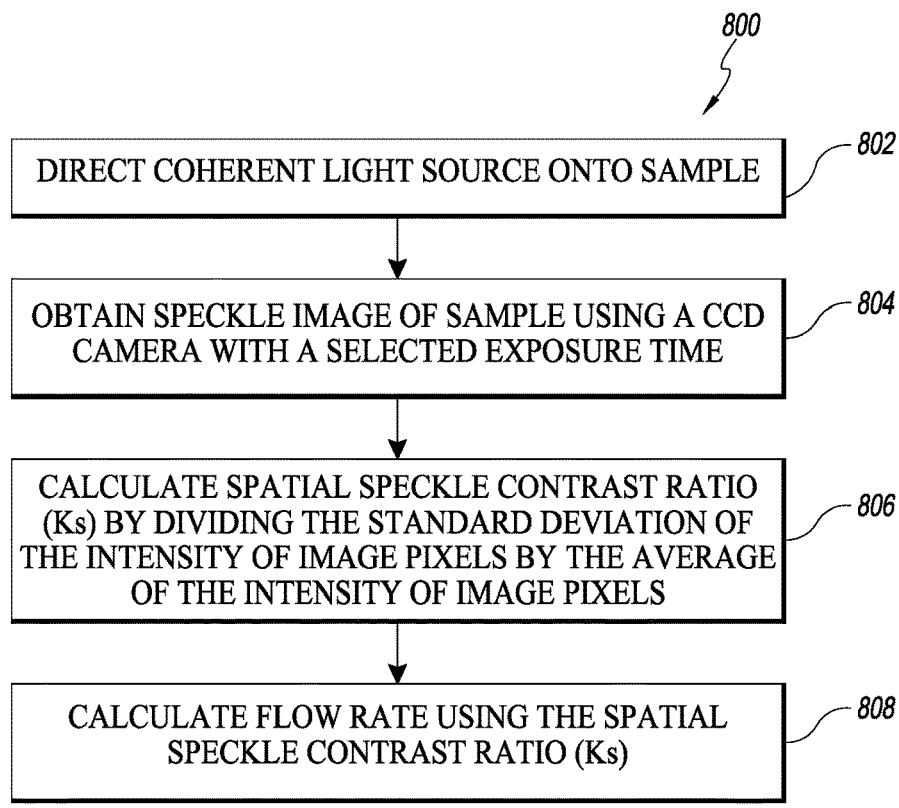
FIG. 8 is a flow diagram of a method for calculating flow rate using spatial domain DSCA.

FIG. 8 is a flow diagram of a method for calculating flow rate using spatial domain DSCA. Process 800 begins in block 802 with directing a coherent light source onto a sample. As noted above, the coherent light source can be, for example, a laser having a long coherence length (i.e., coherence length greater than about 1 mm). Next in block 804 a speckle image of the sample is obtained using a CCD camera with a selected exposure time. The position of the sample at which the image is taken is selected based on the desired penetration depth into the sample of the detected light scattered by deep tissue flow. CCD will capture the image of speckle either by using a relay optics or by placing the CCD chip directly onto the surface of the sample. Process 800 continues in block 806 with calculating the spatial speckle contrast ($K_s$) by dividing the standard deviation of the intensity of image pixels by the average of the intensity of image pixels. In some embodiments, a number of adjacent pixels may be grouped together for a single intensity data point, and standard deviation among the different groups of pixels can be calculated. Similarly, the average intensity among the different groups of pixels can likewise be calculated. Process 800 continues in block 808 with calculating the flow rate using the spatial speckle contrast ($K_s$). As described above, $1/K_s^2$ is related to flow rate in a substantially linear fashion, allowing for computationally trivial calculation of the flow rate. In some embodiments, this approach is used to calculate relative blood flow rate only. In many clinical applications, relative blood flow measurements can be adequate for the task at hand. In other embodiments, this approach can be used to calculate absolute blood flow rate.

Figure 9:
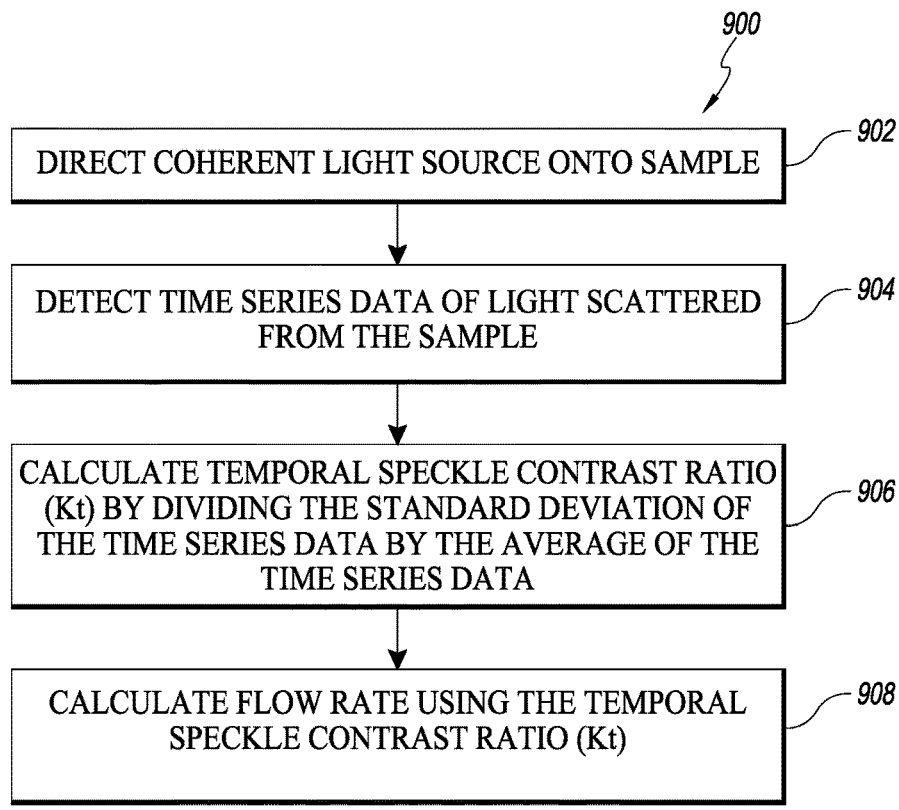
FIG. 9 is a flow diagram of a method for calculating flow rate using time domain DSCA.

FIG. 9 is a flow diagram of a method for calculating flow rate using time domain DSCA. Process 900 begins in block 902 with directing a coherent light source onto a sample. This step can be performed essentially identically to spatial domain DSCA. Next, in block 904, time series data of light scattered from the sample is detected. A detector, for example a CCD camera, CMOS image sensor, an avalanche photodiode, or photomultiplier tube, may be coupled to the sample via a single-mode optical fiber. Intensity measurements may be integrated over a selected exposure time. In some embodiments, the select exposure time can be approximately 1 ms. A series of such measurements are taken sequentially to provide time-series data. Process 900 continues in block 906 with calculating the temporal speckle contrast ($K_t$) by dividing the standard deviation of the time series data by the average of the time series data. In block 908, the flow rate can be calculated using the temporal speckle contrast ($K_t$). As with the spatial speckle contrast ratio, $1/K_t^2$ is related to flow rate in a substantially linear fashion, allowing for the flow rate to be easily calculated. The blood flow rate calculated may be relative flow in some embodiments.

Whether spatial or temporal domain DSCA is selected may depend on a variety of factors. For example, sDSCA relies on the use of a CCD camera or similar imaging device, which is relatively large compared with a single-mode fiber and a photodiode. In some applications, the size difference may pose little obstacle to its use. In applications in which the size of the CCD camera is a limiting factor, a small area sensor may be used and applied directly onto the skin, or a relay optics with small magnification can be used. However, tDSCA does not face the same limitations, and accordingly the temporal domain may be more suitable when space or curvature renders sDSCA impractical. As noted previously, tDSCA provides relatively low time resolution compared to sDSCA, however the tDSCA time resolution is typically adequate for patient monitoring applications, particularly for long-term perfusion monitoring. For short-term monitoring, when time resolution may be more important, sDSCA may be the preferred approach. In both spatial and temporal domains, DSCA provides a technique for measuring blood flow perfusion accurately and quickly, with higher time resolution and lower cost instrumentation than previous methods.

Although this application has been disclosed in the context of certain embodiments and examples, it will be understood by those skilled in the art that the present application extends beyond the specifically disclosed embodiments to other alternative embodiments and/or uses of the application and obvious modifications and equivalents thereof. Additionally, the skilled artisan will recognize that any of the above-described methods can be carried out using any appropriate apparatus. Further, the disclosure herein of any particular feature in connection with an embodiment can be used in all other disclosed embodiments set forth herein. Thus, it is intended that the scope of the present application herein disclosed should not be limited by the particular disclosed embodiments described above.

What is claimed is:

1. A method for determining blood flow characteristics in deep tissue in a patient, the method comprising:
   directing coherent light from a laser light source through an input optical fiber comprising an end positioned directly onto a first location on a skin surface of the patient;
   imaging a second location of the skin surface of the patient via an optical conduit on the skin surface and connected to a detector, wherein a portion of the coherent light is scattered diffusively by the blood flow at a depth of penetration of between 5 mm and 50 mm beneath the patient's skin surface such that the scattered light is at least partially detectable at the second location;
   sending image data from the second location to a software or hardware processor;
   calculating the blood flow characteristics based on the image data of the second location, wherein calculating the blood flow characteristics comprises calculating the speckle contrast by statistically analyzing a probability distribution of intensity fluctuations of the scattered light using the software or hardware processor to determine a temporal speckle contrast ratio ($K_t$) and $1/K_t^2$ values, and correlating the $1/K_t^2$ values with blood flow using the software or hardware processor, wherein calculating the blood flow characteristics comprises using statistical analysis without having to rely on autocorrelation analysis on fast time-series data; and
   signaling the blood flow characteristics calculated from the software or hardware processor to an operator in real time by providing audible, visual, or tactile indicia of the blood flow characteristics.

2. The method of claim 1, wherein the first and second locations are on a patient's limb.

3. The method of claim 1, wherein the first and second locations are on a patient's foot.

4. The method of claim 1, wherein imaging the second location comprises capturing an image with a multi-pixel photodetector.

5. The method of claim 1, wherein the first and second locations are at least 10 mm apart.

6. A method for determining blood flow characteristics in deep tissue in a patient, the method comprising:
   directing coherent light from a laser light source through an input optical fiber comprising an end positioned directly onto a first location of the patient's skin surface;
   imaging a second location of the patient's skin surface via an optical conduit coupled to the skin surface to generate image data, wherein a portion of the coherent light is scattered diffusively by the blood flow at a depth of penetration of between 5 mm and 50 mm beneath the patient's skin surface such that the scattered light is at least partially detectable at the second location;
   calculating the blood flow characteristics using a spatial domain speckle contrast analysis (sDSCA) system, wherein calculating blood flow characteristics comprises statistically analyzing a probability distribution of speckle intensity fluctuations of the image data using a software or hardware processor to determine spatial speckle contrast ratio ($K_s$) and $1/K_s^2$ values, and correlating the $1/K_s^2$ values with blood flow using the software or hardware processor; and
   signaling the blood flow characteristics calculated from the software or hardware processor to an operator by providing audible, visual, or tactile indicia of the blood flow characteristics.

7. The method of claim 6, wherein the first and second locations are on a patient's foot.

8. The method of claim 6, wherein the first and second locations are at least 10 mm apart.

9. A system for assessment of blood flow characteristics in deep tissue, the system comprising:
   a coherent laser light source configured to apply light to the tissue;
   an input optical fiber configured to transmit light from the coherent laser light source, the input optical fiber comprising an end configured to be positioned directly onto a first location of a patient's skin surface;
   a multi-pixel image sensor configured to be in optical communication with a second location of the patient's skin surface and capture optical information including at least a quantity of light transmitted through the skin surface and into tissue, wherein the light is scattered diffusively, at least in part, by the blood flow at a depth of penetration of between 5 mm and 50 mm;
   a hardware or software processor configured to analyze the optical information to determine blood flow characteristics in the tissue by determining a spatial speckle contrast ratio ($K_s$) and $1/K_s^2$ values, wherein the hardware or software processor is further configured to correlate $1/K_s^2$ values with blood flow using the hardware or software processor, and wherein the hardware or software processor is configured to use statistical analysis without having to rely on autocorrelation analysis on fast time-series data; and
   a display configured to provide a signal indicative of the blood flow characteristics determined by the hardware or software processor.

10. The system of claim 9, wherein the multi-pixel image sensor comprises a CCD detector.

11. The system of claim 9, wherein the system is configured to provide the signal indicative of the blood flow in real-time.

12. The method of claim 6, wherein signaling indicative of the blood flow characteristics occurs less than 10 seconds from obtaining the time-series measurements.

13. The method of claim 1, wherein the input optical fiber comprises a multi-mode fiber and the optical conduit comprises a single-mode fiber.

14. The method of claim 6, wherein the input optical fiber comprises a multi-mode fiber, and the one or more sensors is operably connected to a single-mode fiber.

15. The system of claim 9, wherein the input optical fiber comprises a multi-mode fiber and the multi-pixel image sensor is operably connected to a single-mode fiber.

16. The method of claim 1, wherein the blood flow characteristics comprise blood perfusion.

* * * * *